(12) United States Patent
Jaunberzins

(10) Patent No.: US 8,727,772 B2
(45) Date of Patent: *May 20, 2014

(54) ENDODONTIC FILE COMBINING ACTIVE AND PASSIVE CUTTING EDGES

(75) Inventor: Andris Jaunberzins, Franklin, WI (US)

(73) Assignee: William B. Johnson, Tulsa, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/848,688

(22) Filed: Aug. 2, 2010

(65) Prior Publication Data

US 2010/0297578 A1  Nov. 25, 2010

Related U.S. Application Data

(63) Continuation of application No. 11/199,748, filed on Aug. 9, 2005, now Pat. No. 7,766,657.

(51) Int. Cl.
*A61C 5/02* (2006.01)

(52) U.S. Cl.
USPC .......................................................... 433/102

(58) Field of Classification Search
USPC .................... 433/81, 102, 144, 164–166, 224
See application file for complete search history.

(56) References Cited

U.S. PATENT DOCUMENTS

| | | | |
|---|---|---|---|
| 4,260,379 A | 4/1981 | Groves et al. | |
| 4,443,193 A | 4/1984 | Roane | |
| 4,536,159 A | 8/1985 | Roane | |
| 4,934,934 A | 6/1990 | Arpaio, Jr. et al. | |
| 5,106,298 A | 4/1992 | Heath et al. | |
| RE34,439 E | 11/1993 | Heath | |
| 5,380,200 A | 1/1995 | Heath et al. | |
| 5,464,362 A | 11/1995 | Heath et al. | |
| 5,658,145 A | 8/1997 | Maillefer et al. | |
| 5,692,902 A | 12/1997 | Aeby | |
| 5,762,497 A | 6/1998 | Heath | |
| 5,873,719 A | 2/1999 | Calas et al. | |
| 5,897,316 A | 4/1999 | Buchanan | |
| 5,921,775 A | 7/1999 | Buchanan | |
| 5,975,899 A | 11/1999 | Badoz et al. | |
| 6,012,921 A | 1/2000 | Riitano | |
| 6,074,209 A | 6/2000 | Johnson | |
| 6,217,335 B1 | 4/2001 | Riitano et al. | |
| 6,267,592 B1 | 7/2001 | Mays | |
| 6,312,261 B1 | 11/2001 | Mays | |
| 6,315,558 B1 | 11/2001 | Farzin-Nia et al. | |
| 6,390,819 B2 | 5/2002 | Riitano | |
| 6,419,488 B1 | 7/2002 | McSpadden et al. | |

(Continued)

FOREIGN PATENT DOCUMENTS

WO    WO 99/43469 A1    9/1999

OTHER PUBLICATIONS

EP Search Report, Nov. 16, 2006, European Patent.

*Primary Examiner* — Hao D Mai
(74) *Attorney, Agent, or Firm* — Gable Gotwals

(57) ABSTRACT

An endodontic reamer/file for cleaning/shaping a tooth root canal having an elongated shank with a proximal end portion, a distal end and a tapered working portion having a longitudinal axis, the external surface of the shank working portion being defined by a plurality of at least two equally spaced apart continuous concaved helical flutes providing concave flute surfaces, the flute surfaces having therebetween an equal number of spiraled, spaced apart flanges, each flange having in a plane perpendicular the longitudinal axis a single outer end surface having opposed first and second ends, each first end forming an active spiraled leading scraping/cutting edge and each second end forming a passive spiraled edge.

1 Claim, 2 Drawing Sheets

(56) References Cited

U.S. PATENT DOCUMENTS

| | | |
|---|---|---|
| 6,514,076 B1 | 2/2003 | Bleiweiss et al. |
| 6,520,774 B1 | 2/2003 | Mays |
| 6,644,972 B1 | 11/2003 | Mays |
| 6,712,611 B2 | 3/2004 | Garman |
| 6,746,245 B2 | 6/2004 | Riitano et al. |
| 2003/0077553 A1 | 4/2003 | Brock |
| 2004/0023186 A1 | 2/2004 | McSpadden |
| 2004/0043357 A1 | 3/2004 | Garman |
| 2004/0058297 A1 | 3/2004 | Danger |
| 2004/0121283 A1 | 6/2004 | Mason |
| 2005/0272004 A1 | 12/2005 | Desrosiers |
| 2006/0210947 A1 | 9/2006 | Lampert |
| 2006/0216668 A1 | 9/2006 | Scianamblo |
| 2007/0031784 A1 | 2/2007 | Berutti et al. |

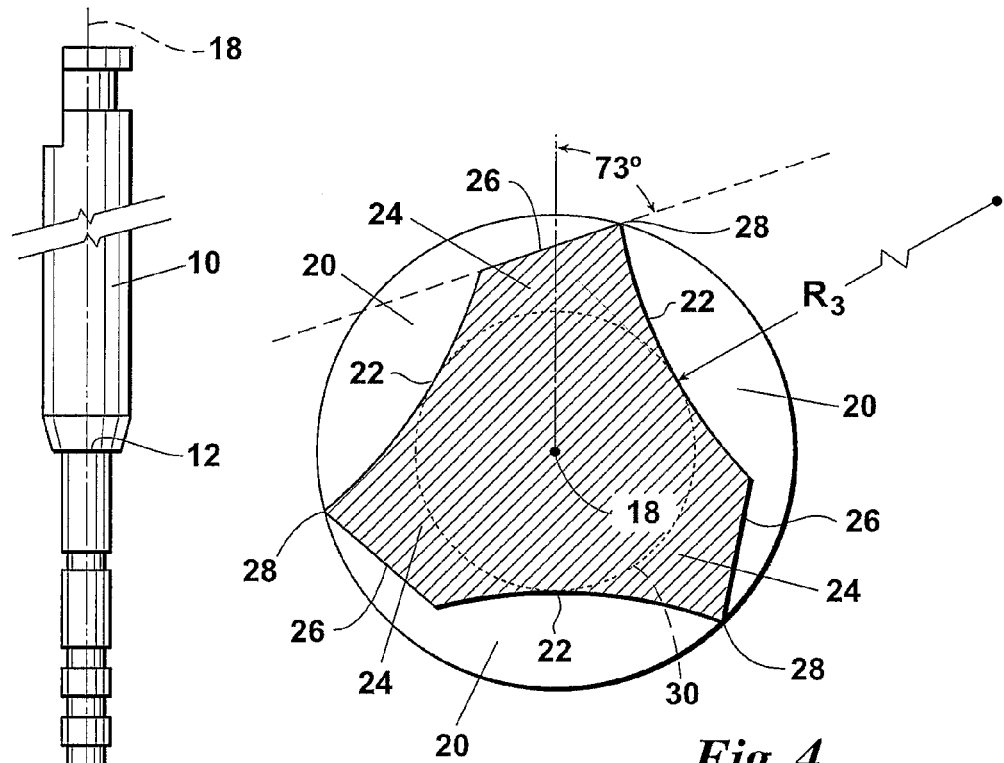
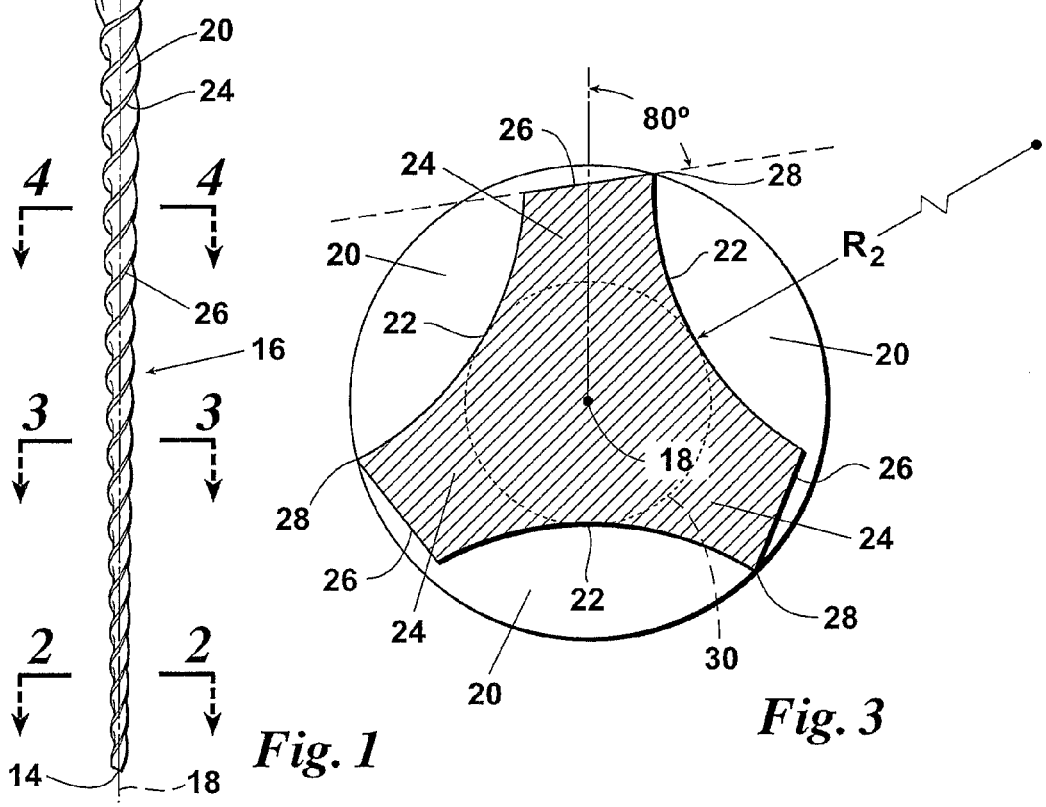
Fig. 1
Fig. 3
Fig. 4

ENDODONTIC FILE COMBINING ACTIVE AND PASSIVE CUTTING EDGES

REFERENCE TO PENDING APPLICATIONS

This application is a continuation application claiming priority to U.S. patent application Ser. No. 11/199,748, filed Aug. 9, 2005, entitled "Endodontic File Combining Active and Passive Cutting Edges", now U.S. Pat. No. 7,766,657.

REFERENCE TO MICROFICHE APPENDIX

This application is not referenced in any microfiche appendix.

BACKGROUND OF THE INVENTION

1. Field of the Invention

This invention relates to a flexible tool that is particularly adaptable for use as an endodontic instrument, most particularly, an endodontic file for use by practitioners in removing the pulpal material from an exposed root of a tooth and for shaping the root canal to receive filler material, such as gutta-percha.

2. Background of the Invention

One of the most significant advancements in dentistry in recent years has been improved treatment of abscessed teeth. In the past a tooth, once abscessed, was usually pulled as the only remedy for alleviating the intense pain. By "abscessed" usually means that the root canal of the tooth becomes infected and the infection causes pressure on the tooth and the nerve endings associated therewith that result in, sometimes, almost unbearable pain. With the advent of endodontics the drastic measure of extracting a tooth that had become abscessed has been eliminated.

The first step in the endodontic treatment of an abscessed tooth is to drill an opening in the crown of the tooth to provide access to the root canal. Once the root canal is exposed, the practitioner then must thoroughly clean the root canal of pulpal material since if the pulpal material is not thoroughly and carefully removed it can be the source of continued infection. Not only is it necessary that the pulpal material be removed but the root canal usually must be shaped in such a way as to permit filling of the root canal with a filler material. While other types of filler materials have been provided still at the present time the most common filler is a paste-like material referred to as "gutta-percha." If the canal is not properly cleaned and shaped the step of filling with gutta-percha may leave void areas that invite the introduction into the root canal of organic matter that can be followed by bacterial action. For these reasons much of the effort of a practitioner to successfully accomplish the endodontic treatment of an abscessed tooth is the cleaning and shaping of the root canal. These steps are accomplished utilizing small diameter tapered files that are inserted by the practitioner through the exposed crown area into the root canal. The canal must be cleaned from the crownal area advancing to the root apex.

A root canal is typically in a tapered configuration, that is, the cross-sectional area of canals is usually greater near the crown of the tooth and is at a minimum at the apex of the tooth, that is, the distal end of the root canal. While the root canal is naturally tapered it is not tapered symmetrically and the canal can have inclusions in intermediate portions between the apex and the crown area that interfere with the passage of filler material. Therefore the root canal must be shaped to remove unnecessary intrusions and to improve the chances that the practitioner can successfully fill the root canal.

Files are usually provided either with a small cylindrical plastic handle portion by which the practitioner manually rotates the files or a shank portion that can be received in the chuck of a dental hand piece by which they are mechanically rotated. In addition to rotation, the practitioner manipulates the files in and out of root canals. "Manipulation" means inserting a file into a canal and reciprocating it to file away intrusions and at the same time to remove pulpal material. Typically the practitioner inserts a file to the point of resistance and then rotates and reciprocates the file to engage spiral scraping edges with the canal wall. The file is then extracted to remove pulpal material and matter scraped from the wall. This procedure is repeated as necessary to clean the entire length of the canal. In the cleaning process the practitioner usually starts with a file of a small diameter and then, as progress is made in cleaning the canal, larger diameter files are employed until the root canal is shaped and cleaned to the apex. Accordingly, endodontic files usually come in sets of standard tapers and varying from smaller to larger diameters. As previously stated, instead of manually rotating an endodontic file the practitioner may insert the file proximal end into the chuck of a hand piece by which the file is mechanically rotated.

Root canals are characteristically not straight. Some root canals curve more than others but few are perfectly straight from the crown to the apex. Therefore it is important that files be flexible so as to be able to follow the natural curvature of the root canal as it is cleaned and shaped from the tooth crown to the tooth apex. If a file is too stiff it can result in the file protruding through a side wall of a tooth root which can introduce an avenue of infection into the tooth. Further, if the file is stiff it is less successful in cleaning the entire area of a canal since the stiffness will cause the file to be deflected drastically to one side of a curve in a canal leaving a portion of the wall that defines the curve unexposed to the action of the file. Therefore, a high degree of flexibility is a desirable characteristic of an endodontic file.

In addition, the strength of a file is very important. In the process of reciprocating and rotating a file in a tooth it is possible for the file to break, leaving a broken part in the tooth. This creates a serious problem for the practitioner. Accordingly, it has long been a desire of the dental profession to have available dental files that are highly flexible and yet strong to resist separation as a result of a torsional twist or pulling action as a file is manipulated within a root canal. The present invention provides a way of substantially increasing the flexibility of dental files while at the same time increasing resistance against torsional or elongational separation.

Historically, all endodontic files had angular cutting surfaces until the introduction of radial land instruments to the art of endodontics (represented by U.S. Pat. No. 4,934,934 to Arpaio, Jr. et al, issued on Jun. 19, 1990).

The use of radial lands prevent active, aggressive cutting of tooth structure, since radial lands circumscribe the circumference of the instruments and prevent moving aggressively into the root canal system. This type of instrument can accurately be described as passive cutting or scraping instruments, as some degree of apical pressure must be asserted by the clinician for it to cut. All other instruments without radial lands could be classified as active cutting instruments. The very nature of a sharp, cutting edge without radial lands will draw the instrument into the canal without pressure being applied by the clinician. More importantly, instruments incorporating radial lands as they rotate will not transport the canal from its original position when instrumenting a curved canal, whereas active cutting instruments by their continued rotation and cutting around a curved canal will transport and tend to straighten the canal.

Active cutting blades are more efficient, in that they enlarge the canal faster. Conversely, passive cutting blades are more inefficient, requiring more time to enlarge the root canal system.

Further, most endodontic files function only in one direction of rotation instead in both directions of rotation. Unidirectional files result in reduced efficiency.

3. Description Of The Prior Art

For background information relating to the subject matter of this invention and specifically relating to dental reamer/files, reference may be had to the following issued United States patents and publications:

| PATENT NUMBER | INVENTOR(S) | ISSUE DATE | TITLE |
| --- | --- | --- | --- |
| 4,443,193 | Roane | Apr. 17, 1984 | Endodontic Instrument |
| 4,536,159 | Roane | Aug. 20, 1985 | Endodontic Instrument |
| 4,934,934 | Arpaio, Jr. et al. | Jun. 19, 1990 | Dental File/Reamer Instrument |
| 5,380,200 | Heath et al. | Jan. 10, 1995 | Endodontic Instrument Of Predetermined Flexibility |
| 5,464,362 | Heath et al. | Nov. 07, 1995 | Endodontic Instrument |
| 5,658,145 | Maillefer et al. | Aug. 19, 1997 | Set Of Instruments For Boring Dental Radicular Canals And Method Therefor |
| 5,692,902 | Aeby | Dec. 02, 1997 | Set Of Instruments For The Boring Of Radicular Dental Canals |
| 5,873,719 | Calas et al. | Feb. 23, 1999 | Dental Reamer |
| 5,897,316 | Buchanan | Apr. 27, 1999 | Endodontic Treatment System |
| 5,921,775 | Buchanan | Jul. 13, 1999 | Endodontic Treatment System |
| 5,975,899 | Badoz et al. | Nov. 02, 1999 | Dental Reamer |
| 6,012,921 | Riitano | Jan 11, 2000 | Endodontic Systems For The Anatomical, Sectional And Progressive Corono-Apical Preparation Of Root Canals With Three Sets Of Dedicated Instruments |
| 6,074,209 | Johnson | Jun. 13, 2000 | Reduced Torque Endodontic File |
| 6,217,335 | Riitano et al. | Apr. 17, 2001 | Endodontic Systems And Methods For The Anatomicall, Sectional And Progressive Corono-Apical Preparation Of Root Canals With Minimal Apical Intrusion |
| 6,267,592 | Mays | Jul. 31, 2001 | Highly Flexible Instrument For Dental Applications |
| 6,312,261 | Mays | Nov. 06, 2001 | Endodontic Obturator With Removable Carrier And Method Of Use Thereof |
| 6,315,558 | Farzin-Nia et al. | Nov. 13, 2001 | Method Of Manufacturing Superelastic Endodontic Files And Files Made Therefrom |
| 6,390,819 | Riitano | May 21, 2002 | Endodontic Systems And Methods For The Anatomical, Sectional And Progressive Corono-Apical Preparation Of Root Canals With Dedicated Stainless Steel Instruments And Dedicated Nickel/Titanium Instruments |
| 6,419,488 | McSpadden et al. | Jul. 16, 2002 | Endodontic Instrument Having A Chisel Tip |
| 6,514,076 | Bleiweiss et al. | Feb. 04, 2003 | Precipitation Hardenable Stainless Steel Endodontic Instruments And Methods For Manufacturing And Using The Instruments |
| 6,520,774 | Mays | Feb. 18, 2003 | Highly Flexible Instrument For Medical Applications |
| 6,644,972 | Mays | Nov. 11, 2003 | Endodontic Obturator With Removable Carrier And Method Of Use Thereof |
| 6,746,245 | Riitano et al. | Jun. 08, 2004 | Methods For Cleaning And Shaping Asymmetrical Root Canals In An Anatomical Fashion |
| 2004/0121283 | Mason | Jun. 24, 2004 | Precision Cast Dental Instrument |
| 2003/0077553 | Brock | Apr. 24, 2003 | Endodontic Instrument Having Notched Cutting Surfaces |
| 2004/0058297 | Danger | Mar. 02, 2004 | Root Canal Instrument |
| 2004/0043357 | Garman | Mar. 04, 2004 | Endodontic Instrument |
| 2004/0023186 | McSpadden | Feb. 05, 2004 | Multi-Tapered Endodontic File |
| Re. 34,439 | Heath | Nov. 09, 1993 | Dental Compactor Instrument |

BRIEF SUMMARY OF THE INVENTION

This invention herein is a dental reamer/file that is for use in performing endodontic procedures, that is, specifically, cleaning and shaping the root canal of a tooth to prepare the tooth to receive a filler material, such as gutta percha.

The invention is specifically a file which may be manipulated manually or by machine, that is, a hand piece that is commonly used by endodontic practitioners. The file includes an elongated shank with a proximal end, a distal end and a tapered working portion that extends from the proximal portion to the distal end. The shank also includes either an enlarged diameter handle portion, typically made of plastic for manually manipulating the file or a smaller diameter metal chuck stem, usually integral with the file, that is configured to be received in a dental hand piece by which the file is mechanically rotated and can be manipulated by the practitioner.

The external surface of the shank working portion is defined by a plurality of at least two spaced apart continuous concaved helical flutes that extend into the central core portion. Spaced between the helical flutes are an equal number spiraled spaced apart flange portions. Each flange portion has, in a plane perpendicular the file longitudinal axis, a single outer surface having opposed first and second ends at intersections with the concave flute surfaces. The first end intersection forms a continuous spiral leading edge that extends the length of the shaft working portion.

In one embodiment each flange outer end surface is perpendicular to a radius drawn from the rotational axis of the shank working portion. In this embodiment bi-directional scraping edges, each having a positive rake angle, are achieved. In the preferred embodiment of the invention the flange outer end surface varies at different locations along the length of the elongated shank tapered working portion.

In other embodiments each flange outer end is a straight line that intersects a radius drawn from the rotational axis of the shank working portion at an angle. These embodiments produce an endodontic file having a positive rake angle at one end of each flange outer end and a negative rake angle at the opposite end.

In other embodiments of the invention the radius of curvature of the concave flute surfaces vary at different locations along the length of the elongated shank tapered working portion. When the radius of curvature of a concave flute surface is relatively short it means that the flute is of a relatively deeper depth. This configuration means that the total cross-sectional area of the shank is relatively reduced, resulting in increased flexibility of the file but at the same time resulting in decreased torsional resistance. By varying the depth of concavity of the flute areas the total cross-sectional area can be varied to thereby provide variable flexibility along the length of the file. Further the shank outer surface can vary to provide variable rake angles. Using the concept of this invention the rake angles and flute depths can vary in relation to each other along the length of a file to thereby provide a file that is optimally designed to achieve maximum flexibility where flexibility is important and maximal torque resistance where this aspect of the file is important.

A more complete understanding of the invention will be obtained from the following detailed description of the preferred embodiments and claims, taken in conjunction with the attached drawings.

BRIEF DESCRIPTION OF THE DRAWINGS

FIG. 1 is an elevational view of an endodontic file of the type that can be used to incorporate the principles of this invention. The file illustrated in FIG. 1 is the type having a chuck stem at the proximal end that can be received in the chuck of a dental hand piece by which the file is mechanically rotated. The hand piece is also used by the practitioner to manipulate the file in and out of a root canal as it is mechanically rotated.

FIG. 3 is cross-sectional view taken along the line 3-3 of FIG. 1 and showing an alternate embodiment of the file cross-sectional configuration. In this arrangement the outer end surface of each of the three flange portions is a straight line that is at an angle of 80° relative to a radius drawn from the rotational axis of the file.

FIG. 4 is a cross-sectional view like that of FIG. 3 but in two ways that are different. First, in FIG. 3 the radius of curvature of the concave surface of each flute is of a median diameter indicated by the numeral $R_2$ wherein in FIG. 4 the radius of curvature of each flute is greater, indicated by the numeral $R_3$. The flute concave surface being of a greater radius of curvature in FIG. 4 means that the total cross-sectional area of the file is increased which means reduced flexibility but at the same time increased torsional resistance. Another difference in FIG. 4 compared to FIG. 3 is that the planar end surface of each flange portion intersects a radius of the file drawn through its rotational axis at an angle of 73°.

DETAILED DESCRIPTION OF THE PREFERRED EMBODIMENTS

Figure 2:
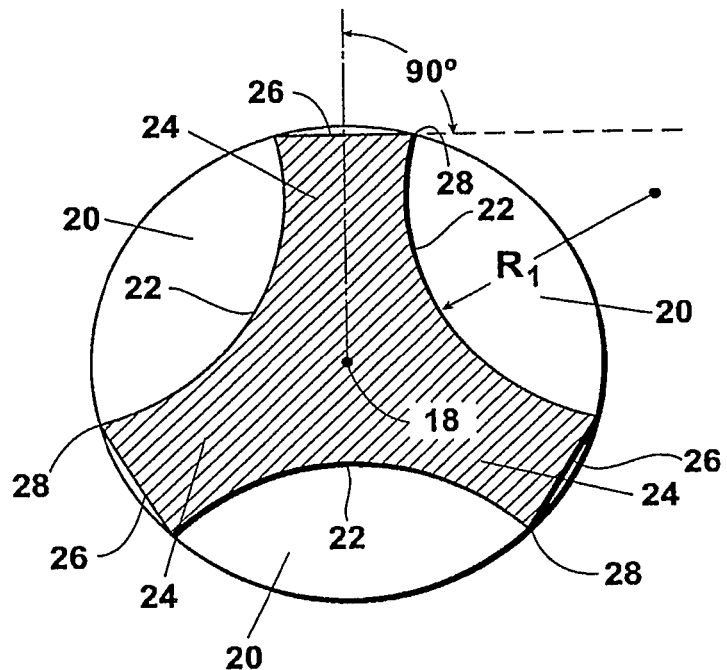
FIG. 2 is a cross-sectional view taken along the line 2-2 of FIG. 1. This figure shows a cross-sectional view wherein the file has three spaced apart helical flutes each with a semi-circular cross-sectional contour and three integral flange portions that extend between the flutes. The outer end surface of each flange portion is a straight edge that intersects a radius drawn from the file rotational axis at an angle of 90°.

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10 | Chuck stem |
| 12 | Proximal end |
| 14 | Distal end |
| 16 | Shaft working portion |
| 18 | Longitudinal rotational axis |
| 20 | Flute |
| 22 | Flute surface |
| 24 | Flange |
| 26 | Flange end surface |
| 26A | Arcuate end surface |
| 28 | Scraping/cutting edge |

Referring to the drawings and first to FIG. 1, an elevational view illustrates a typical endodontic file. The file includes a chuck stem 10 that is at a proximal end 12 of the file. The distal end 14 is of substantially reduced diameter compared to the proximal end 12. Intermediate proximal end 12 and distal end 14 is an elongated shank working portion generally indicated by the numeral 16.

Chuck stem 10 is typically integrally formed with the metal file and is configured to be received in a chuck (not shown) of a dental hand piece by which the file is rotated and by which the file can be manipulated in and out of a root canal by an operator. Chuck stem 10 can be replaced by a small plastic handle portion configured for manual manipulation by an endodontic practitioner. Whether a chuck stem or a handle portion is used is irrelevant to the invention herein and the specific configuration of chuck stem 10 is not part of the invention. Instead, an important aspect of the present invention is the configuration of the external surface of the file shaft working portion 16. This configuration is illustrated in the cross-sectional views of FIGS. 2, 3 and 4.

FIG. 2 is a cross-sectional view taken along the line 2-2 of FIG. 1. The plane of this cross-sectional view is perpendicular to a longitudinal axis 18 of the file working portion 16 which also is the longitudinal axis of the chuck stem 10. This longitudinal axis is also termed a rotational axis as it is the axis at which file working portion 16 is rotated when positioned within a tooth root canal. Rotational axis 18 is seen in each of the cross-sectional views. Formed on the exterior surface of shaft working portion 16 are a plurality of at least two helical flutes 20. In the illustrated arrangement there are three spaced apart helical flutes 20. These helical flutes are formed into the exterior surface of the file working portion 16. Each helical flute has a flute surface 22. While three helical flutes 22 are illustrated, the file can be manufactured with only two flutes or can be manufactured with more than three flutes. As a practical consideration, however, the file is typically made with two or three flutes with three flutes being ideal. While four flutes could be employed, the additional flutes serve to increase the complexity of manufacture without adding significantly to the performance of the tool. Thus, for all practical purposes, the ideal file construction that incorporates the principles of this invention will employ three flutes 20. These flutes provide three helical flanges 24.

Each of the helical flanges 24 has, at the outer end thereof, an end surface 26. Each end surface 26 contacts, in cross-sectional views, opposed flute surfaces. In the embodiment of FIG. 2, a continuous spiraled scraping/cutting edge 28 is formed at the outer end of each end surface 26, that is, where each end surface 26 contacts an opposed flute surface 22. In FIG. 2, end 28 of each end surface 26 forms a helical scraping/cutting edge.

In the embodiment of FIG. 2 one half of the helical scraping/cutting edges 28 becomes leading edges when the tool is rotated clockwise and the other half become leading edges when the tool is rotated counterclockwise. In FIG. 2 all of the leading edges are equally effective so that in this embodiment the tool functions essentially the same whether it is rotated clockwise or counterclockwise. However, in actual practice, there is a difference in the action of the tool between clockwise and counterclockwise direction. With helical flutes and helical flanges when the tool is rotated clockwise there is a tendency to thread the file into the root canal whereas when rotated counterclockwise there is a tendency to thread the file out of the root canal. An endodontic practitioner takes advantage of these characteristics to effectively clean and shape a root canal.

Figure 2A:
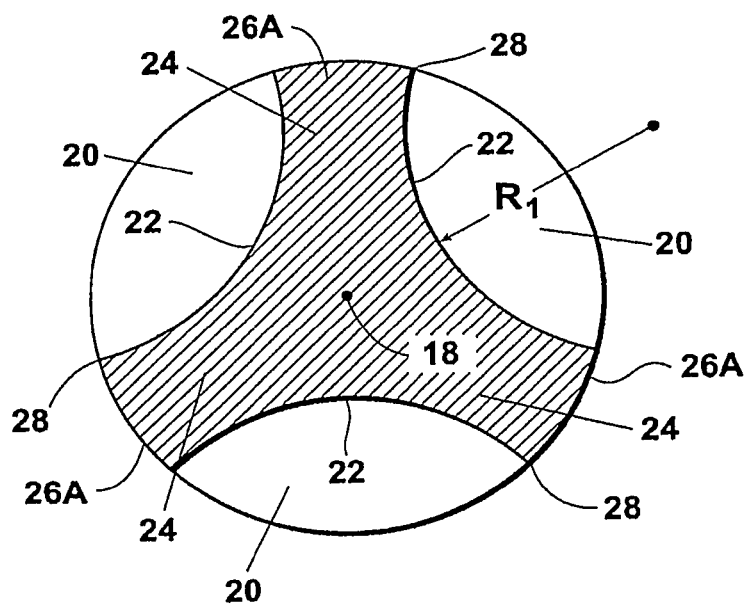
FIG. 2A is a cross-sectional view like that of FIG. 4 but different in that the outer end surface of each of the flange portions is not straight as in FIG. 2 but is arcuate, that is, a curve that circumscribes the circumference of the file. This surface prevents this portion of the file from moving into the root canal wall, that is, it provides a passive surface at this part of the file length.

FIG. 2A shows a file cross-sectional structure in which angular cutting surfaces are not employed but instead radial lands 26A are provided at the outer end of each of the flange portions. These radial lands 26A prevent this portion of the file moving into the root canal wall. Specifically, the radial lands 26A provide passive surfaces on this part of the file length.

FIG. 3 shows an alternate embodiment of the invention in which the outer end 26 of each helical flange 24 is at an angle to a radius drawn midway through each helical flange. While FIG. 2 shows a cross-sectional arrangement in which end surfaces 26 are at a 90° angle relative to a radius drawn through axis 18, in FIG. 3 end surface 26 is at an angle of about 80° relative to an axis. FIG. 4 is similar to FIG. 3 except that the end surfaces 26 are each at an angle of 73° relative to a radius drawn through axis 18 and the center of each of helical flanges 24.

Whereas in FIG. 2 there is a helical scraping/cutting edge 28 at each end of each of the end surface 26 in the embodiments of FIGS. 3 and 4, due to the angle of each end surface 26 relative to a radius of the file, there is only a single active scraping/cutting edge 28, and a corresponding passive scraping/cutting edge. That is, for example with respect to FIG. 3, when the tool is rotated clockwise each of the forward scraping/cutting edges 28 engage the surface of the root canal to cut or scrape away portions of the canal to thereby clean and shape the canal while the trailing edges do not contact the root canal and therefore are not involved with scraping/cutting action. That is, FIG. 3 is a file design having active and passive cutting/scraping edges 28. When the file of FIG. 3 is rotated counterclockwise, a scraping/cutting edge 28 contacts the root canal but at a negative cutting angle so edge 28 does not tend to cut into but functions essentially to perform a scraping action. The same is even more true for the arrangement of FIG. 4.

There are two basic differences in the cross-sectional arrangements of each of FIGS. 2, 3 and 4 compared to the others. The first difference that has been discussed is the angle of each helical end surfaces 26 relative to a radius extending midway through each helical flange portion 24. A second difference is the radius of curvature of each flute surface 22. For instance in FIG. 2, the curvature of each flute surface 22 is formed by a relatively short radius $R_1$. In FIG. 3 flute surfaces 22 is defined by a longer radius $R_2$. FIG. 4 employs an even longer radius $R_3$. Changing the radius of curvature of flute surfaces 22 affects scraping/cutting edges 28. Changing the angle of end surfaces 26 also affects scraping/cutting edges 28. In any three cross-sectional embodiments of FIGS. 2, 3 and 4 the scraping/cutting edges 28 all have a slightly positive cutting angle. However, the sharpness of the cutting edges remains about the same in each of the three figures. Selection of the angle of the cutting edge can be adjusted in two ways, that is, by adjusting the angle of the end surfaces 26 and adjusting the depth of flutes 20.

A change in the depth of the flutes 20 changes the cross-sectional area of the file and accordingly the torsional strength at any selected cross-sectional point. Thus the designer of an endodontic file incorporating the principles of this invention can vary in the helical flute depth and the angle of the helical end surfaces to achieve a file having active and passive scraping/cutting edges, selected cutting angle action, flexibility and torque resistance.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An endodontic instrument comprising at least a first and a second transverse sections, each of different cross-sectional area and different shape than the other and located along a length of a tapered working portion of the endodontic instrument, the first transverse section being located nearer a tip end of endodontic instrument than the second transverse section, the first and second transverse sections each including at least three arcuate-shaped flute surfaces, the at least three arcuate-shaped flute surfaces of the first and second transverse sections forming a central core portion of the tapered working portion of the endodontic instrument;

wherein each arcuate-shaped flute surface intersecting with an adjacent flange end surface, forming a single cutting edge which is an active cutting edge having a positive rake angle when the endodontic instrument is rotated in one direction and a passive cutting edge having a negative rake angle when the instrument is rotated in an opposite direction, wherein the different shapes of the first and second transverse sections being defined in part by an angle of the flange end surface of each transverse section, the angle of the flange end surface being between the flange end surface and a radius drawn from a rotational axis of the endodontic instrument at an angle of 90 degree; and wherein each arcuate-shaped flute surface being defined by a radius R, the radius R selected to provide a concave-shaped flute surface, the radius R of the at least three arcuate-shaped flute surfaces of the first transverse section being a shorter radius than that of the at least three arcuate-shaped flute surfaces of the second transverse section, the radius R and the angle of the flange end surface of each transverse section being selected to define the positive rake angle, the positive rake angle of the first transverse section being a different rake angle than the positive rake angle of the second transverse section.

* * * * *